United States Patent [19]

Iwata et al.

[11] Patent Number: 4,594,424
[45] Date of Patent: Jun. 10, 1986

[54] 5-MERCAPTO-1,2,3-THIADIAZOLES COMPOSITION AND PROCESS FOR PREPARING THE SAME

[75] Inventors: Fumio Iwata; Takato Nakamura; Tadakazu Sakata, all of Ube, Japan

[73] Assignee: UBE Industries, Ltd., Ube, Japan

[21] Appl. No.: 629,360

[22] Filed: Jul. 10, 1984

[30] Foreign Application Priority Data

Jul. 12, 1983 [JP] Japan ................... 58-125592

[51] Int. Cl.$^4$ .......................... C07D 285/06
[52] U.S. Cl. ........................... 548/127
[58] Field of Search ........................... 548/127

[56] References Cited

U.S. PATENT DOCUMENTS

| | | | |
|---|---|---|---|
| 4,012,382 | 3/1977 | Bouzard et al. | 548/127 |
| 4,113,733 | 9/1978 | Kruger | 260/306.8 |
| 4,340,742 | 7/1982 | Kruger | 548/127 |
| 4,380,639 | 4/1983 | Crenshaw et al. | 548/135 |
| 4,454,336 | 6/1984 | Curran et al. | 548/127 |
| 4,540,794 | 9/1985 | Sakai et al. | 548/127 |

FOREIGN PATENT DOCUMENTS

| | | | |
|---|---|---|---|
| 103840A | 3/1984 | European Pat. Off. | |
| 2601700 | 7/1976 | Fed. Rep. of Germany | 548/164 |
| 23974 | 3/1978 | Japan | |
| 0011977 | 1/1982 | Japan | 548/127 |
| 51271 | 3/1984 | Japan | |
| 39884 | 3/1984 | Japan | |
| 95282 | 6/1984 | Japan | |

Primary Examiner—Maurice J. Welsh
Assistant Examiner—Garnette D. Draper
Attorney, Agent, or Firm—Frishauf, Holtz, Goodman & Woodward

[57] ABSTRACT

There is disclosed a 5-mercapto-1,2,3-thiadiazoles composition comprising a 5-mercapto-1,2,3-thiadiazole combined with (A) one or more compounds selected from the group consisting of water, an alcohol, an aromatic hydrocarbon and a halogenated hydrocarbon and (B) a halide of an alkali metal and process for preparing the same.

Said composition can remarkably reduce the explosiveness of a 5-mercapto-1,2,3-thiadiazole to make its handling easy and to make it usable for various applications with a sense of security, for example, for manufacturing pharmaceuticals and agricultural chemicals.

19 Claims, No Drawings

5-MERCAPTO-1,2,3-THIADIAZOLES COMPOSITION AND PROCESS FOR PREPARING THE SAME

This invention relates to a 5-mercapto-1,2,3thiadiazoles composition having reduced the explosiveness of 5-mercapto-1,2,3-thiadiazoles (1,2,3-thiadiazole-5thiols) and a process for preparing the same.

A 5-mercapto-1,2,3-thiadiazole is a chemical material having a wide application and has an important application as an intermediate, particularly for pharmaceuticals, agricultural chemicals and so on.

However, since a 5-mercapto-1,2,3-thiadiazole is explosive, that there is a high possibility that it causes an unexpected accident during manufacturing, storage and transportation thereof. Hence, it is a compound accompanied by difficulties in the handling. Therefore, there has conventionally been a disadvantage that serious attention should necessarily be paid in the handling thereof and that the compound could not be used for various applications with a sense of security.

In view of such circumstances, the present inventors have made extensive studies for the purpose of reducing remarkably the explosiveness of a 5-mercapto-1,2,3,-thiadiazole to make its handling easy and to make it usable for various applications with a sense of security. As a result, the present inventors have found that the purpose can be attained by combining a 5mercapto-1,2,3-thiadiazole with a specific compound or compounds so that it can be used without any difficulty for various applications, for example, for manufacturing pharmaceuticals and agricultural chemicals, and have accomplished the present invention.

This invention relates to a 5-mercapto-1,2,3-thiadiazoles composition having reduced the explosiveness of a 5-mercapto-1,2,3-thiadiazole comprising a 5-mercapto-1,2,3-thiadiazole combined with (A) one or more compounds selected from the group consisting of water, an alcohol, an aromatic hydrocarbon and a halogenated hydrocarbon and (B) a halide of an alkali metal, and a process for preparing the same.

In the present specification, the term "5-mercapto-1,2,3-thiadiazole" includes, needless to say, a 5-mercapto-1,2,3-thiadiazole and its salt of an alkali metal such as sodium salt, potassium salt and the like as well as its hydrate and so on.

The amounts of the compound of (A) and the compound of (B) to be combined with the 5-mercapto-1,2,3-thiadiazole may freely be varied depending upon the purpose of use of the 5-mercapto-1,2,3-thiadiazole. However, in order to make a composition which has sufficiently low explosiveness for the use of many chemical reactions, the content in the composition of the compound of (A) is typically 5 to 25% by weight, preferably 10 to 20% by weight, and the content of the compound of (B) is 10 to 30% by weight, preferably 15 to 25% by weight. If the contents of the compound of (A) and the compound of (B) are excessively high, there sometimes are difficulties in using the 5-mercapto-1,2,3-thiadiazole for the same applications as mentioned above, and if the contents thereof are excessively low, the reduction of the explosiveness sometimes becomes insufficient. Therefore, it is desirable that the contents of the compound of (A) and the compound of (B) to be combined with the 5-mercapto-1,2,3-thiadiazole should be within the range mentioned above.

In the present invention, there may advantageously be used a saturated aliphatic alcohol, preferably a lower alcohol having 1 to 4 carbon atoms such as methyl alcohol, ethyl alcohol, n-propyl alcohol, isopropyl alcohol, n-butyl alcohol, sec-butyl alcohol, t-butyl alcohol for the alcohol in the compound of (A); a loweralkylbenzene such as benzene, toluene, ethylbenzene, xylene, mesitylene for the aromatic hydrocarbon; and methylene chloride, chloroform, carbon tetrachloride and the like for the halogenated hydrocarbon. The compound of (A) may be used in single or in combination of two or more kinds thereof. Among the compound of (A), water and/or a saturated aliphatic alcohol may especially preferably be used.

As the halides of an alkali metal in the compound of (B), there may advantageously be used a chloride and a bromide such as sodium chloride, potassium chloride, sodium bromide and potassium bromide. The halide of an alkali metal may also be used in single or in combination of two or more kinds thereof, and among the halide of an alkali metal, sodium chloride and potassium chloride may preferably be used.

In the preparation of the 5-mercapto-1,2,3-thiadiazoles composition according to the present invention, a method may be used in which, a 5-mercapto-1,2,3-thiadiazole is once isolated from the manufacturing step of the 5-mercapto-1,2,3-thiadiazole to obtain the same followed by combining the compound of (A) and the compound of (B); and may also be prepared by a method in which the 5-mercapto-1,2,3-thiadiazole is not isolated from the manufacturing step followed by combining the compound of (A) and the compound of (B). The time, means and so on for combining the compound of (A) and the compound of (B) are not particularly limited and the 5-mercapto-1,2,3-thiadiazoles composition according to the present invention may be prepared by any method. Further, the 5-mercapto-1,2,3-thiadiazole to be used for manufacturing the composition according to this invention may be any one prepared by any method.

As the method for preparing the 5-mercapto-1,2,3-thiadiazole to be used in the present invention, there may be mentioned, for example, a method in which a trihaloacetaldehyde and a hydrazine are subjected to condensation reaction in a solvent, followed by the reaction of the resulting reaction product with a sulfide, a hydrosulfide and a combination of a base and hydrogen sulfide (see Japanese Unexamined Patent Publications No. 95282/1984 and No. 51271/1984); a method and subsequent optional addition of a halogen to the resulting reaction mixture (see Japanese Patent Application No. 167577/1983) in which a trihaloacetaldehyde and a carboalkoxyhydrazine or a dithiocarboalkoxyhydrazine are subjected to reaction in a solvent, followed by the reaction of the resulting product with a sulfide, a hydrosulfide and a combination of hydrogen sulfide and a base (see Japanese Patent Application No. 157234/1983); a method disclosed in Japanese Unexamined Patent Publication No. 39884/1984; a method disclosed in Japanese Unexamined Patent Publication No. 23974/1978; and a method disclosed in J. Heterocyclic Chem. 15, 1295 (1978); a method disclosed in Tetrahedron Letters, 26, 2398(1973).

As a concrete example for a method of manufacturing the 5-mercapto-1,2,3-thiadiazoles composition according to the present invention, there may be mentioned, for example, a method which comprises mixing a 5-mercapto-1,2,3-thiadiazole and a halide of an alkali metal of the compound of (B), subsequently adding an excess amount of the compound of (A), condensing the mixture to remove the excess amount of the compound of (A) by evaporation to dryness. This method, however, is accompanied by danger of explosion during the operation such as condensation and evaporation to dryness. Therefore, this method cannot be said to be good for manufacturing the composition according to the present invention.

Further, there may be mentioned a method in which a 5-mercapto-1,2,3-thiadiazole and the halide of an alkali metal of (B) are dissolved in the compound of (A); the resulting solution is concentrated as occasion demands and then cooled to cause precipitation. According to this method, however, there is a small disadvantage that the yield of the composition according to this invention obtained by the precipitation is low.

The present inventors have made extensive studies to develop a suitable manufacturing method capable of producing industrially and advantageously the composition according to this invention with safety and in high yield. As the result, the present inventors have found that the composition according to this invention can easily and advantageously be isolated and obtained with safety by adding the halide of an alkali metal of (B) to a solution containing a 5-mercapto-1,2,3-thiadiazole in the compound of (A) followed by salting out to precipitate the present composition according to this invention.

In a preferable and suitable manufacturing method for the composition according to this invention, the solution containing a 5-mercapto-1,2,3-thiadiazole in the compound of (A) may be prepared by way of any method. For instance, the composition may be prepared by a method (1) in which the compound of (A) is added to the 5-mercapto-1,2,3-thiadiazole for dissolution. However, it is particularly preferable to prepare the composition by a method (2) which comprises reacting a trihaloacetaldehyde with a hydrazine using as a solvent the compound of (A), preferably water and/or an aliphatic saturated alcohol; adding a sulfide, hydrosulfide or a base and hydrogen sulfide to the resulting reaction mixture to cause cyclization reaction; removing, from the thus obtained reaction mixture containing a 5-mercapto-1,2,3-thiadiazole, impurities, for example, an inorganic salt and the like formed and precipitated by side reactions to obtain a solution containing a 5-mercapto-1,2,3-thiadiazole in the compound of (A), since there are great advantages in that the starting material for preparing the 5-mercapto-1,2,3-thiadiazole has higher chemical stability and is less expensive as compared with conventional raw materials for preparing a 5-mercapto-1,2,3-thiadiazole; the 5-mercapto-1,2,3-thiadiazole can easily and simply be produced; there is no loss of the reaction product which loss accompanies the isolation operation; and the solvent used for manufacturing the 5-mercapto-1,2,3-thiadiazole can effectively be utilized for the composition according to this invention. It should be noted that the 5-mercapto-1,2,3-thiadiazole obtained by the above mentioned method (2) is contained in the form of a salt.

In the above-mentioned method (2), as a trihaloacetaldehyde, chloral, chloralhydrate tribromoacetaldehyde, triiodoacetaldehyde and the like are effective, and among these the trichloroacetaldehydes such as chloral and chloral hydrate are preferred. As the hydrazine, are effective a hydrazine compound having an arylsulfonyl group such as p-toluenesulfohydrazide, benzenesulfohydrazide, p-xylenesulfohydrazide and the like; a hydrazine compound having an alkyl sulfonyl group such as methanesulfohydrazide, ethanesulfohydrazide and the like; and a hydrazine compound having a nitrosubstituted aryl group such as 2,4-dinitrophenylhydrazine.

The condensation reaction of the trihaloacetaldehyde and the hydrazine proceeds quantitatively and a trihaloacetaldehyde hydrazone compound of the following formula is produced:

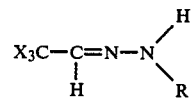

wherein X is a halogen atom in the trihaloacetaldehyde used; and R is an arylsulfonyl group, and an alkylsulfonyl group, a nitro-substituted aryl group and the like in the hydrazine used.

Equimolar amounts of the trihaloacetaldehyde and the hydrazine may be used. However, in order to complete the reaction, it is preferable to use a slightly excess amount of the hydrazine, generally around 1.1 molar times of the amount of trihaloacetaldehyde. The reaction temperature is between $-20°$ and $50°$ C., preferably between 0 and $10°$ C., and the reaction time is not particularly limited but it is generally between 0.5 and 3 hours. As the solvent, the above-mentioned compound of (A) may advantageously be employed.

It is preferable that the reaction product obtained by the condensation reaction of a trihaloacetaldehyde and a hydrazine in a solvent is subjected, without isolation of the reaction product from the reaction mixture, to cyclization reaction by adding a sulfide salt, a hydrosulfide salt or a base and hydrogen salfide to the reaction mixture containing the reaction product, since the operation can be simplified; there is no loss of the reaction product accompanying the isolation operation; and the solvent used in the condensation reaction becomes as such the solvent for a cyclization reaction to be utilized as one component for the composition according to this invention. In the cyclization reaction, in cases where a sulfide, a hydrosulfide and the like are used, a base is not particularly needed, the cyclization reaction (formation of a 5-mercapto-1,2,3-thiadiazole) may be carried out by adding a base. The reaction temperature at the time when the cyclization reaction is conducted is not higher than $100°$ C., preferably between $-10°$ and $40°$ C. Generally the cyclization reaction is completed in 2 to 5 hours and a 5-mercapto-1,2,3-thiadiazole salt is formed.

As the sulfide salt, there may be mentioned a sulfide salt of an alkali metal and an alkaline earth metal such as sodium sulfide, potassium sulfide, rubidium sulfide, lithium sulfide, calcium sulfide, barrium sulfide, strontium sulfide, magnesium sulfide and the like, ammonium sulfide and so on. As the hydrosulfide salt, there may be mentioned a hydrosulfide salt of an alkali metal and an alkali earth metal such as sodium hydrosulfide, potassium hydrosulfide, calcium hydrosulfide and the like, ammonium hydrosulfide and so on. The amount of the sulfide salt or the hydrosulfide salt to be used is typically 1 to 5 moles, preferably 2 to 3 moles per one mole of the reaction product of the condensation reaction (a trihaloacetaldehyde hydrazone compound). The base is necessarily used when hydrogen sulfide is used. As the base, there may be mentioned an alkali metal salt such as sodium hydroxide and potassium hydroxide; a metal alcoholate such as sodium methoxide, sodium ethoxide, potassium methoxide, potassium ethoxide, calcium ethoxide and aluminium ethoxide; a metal amide such as sodium amide, lithium amide, potassium amide and rubidium amide; an amine compound such as hexamethylenetetramine and so on. The base may suitably be used in an amount of 2 to 10 moles, preferably 3 to 5 moles per one mole of the reaction product obtained by the condensation reaction.

The amount to be used of the hydrogen sulfide may suitably be 2 to 15 moles in general, preferably 2.5 to 10 moles per one mole of the reaction product obtained by the condensation reaction.

When such an impurity as by-product is removed from the reaction mixture containing a 5-mercapto-1,2,3-thiadiazole by way of a method known per se such as filtration, and as occasion demands insolubles are removed by further condensing to obtain a solution containing the 5-mercapto-1,2,3-thiadiazole combined with the compound of (A) can be obtained. A solution containing a 5-mercapto-1,2,3-thiadiazole in the compound of (A) which may be more preferably used, can be obtained when the reaction mixture is treated with an activated carbon after removal of impurities at the time of a solution containing a 5-mercapto-1,2,3-thiadiazole in the compound of (A) according to the method (2). The treatment with an activated carbon may be carrie out either before or after concentration. With respect to a method for preparing a 5-mercapto-1,2,3-thiadiazole according to the method (2), the present applicant proposed a process for preparing a 5-mercapto-1,2,3-thiadiazole in above-mentioned Japanese Unexamined Patent Publication No. 95282/1984.

In the preferred method for preparing the composition according to the present invention, it is desirable that the concentration of the solution containing the 5-mercapto-1,2,3-thiadiazole in the compound of (A) may be adjusted to 3 to 20% by weight, preferably 5 to 15% by weight, since the composition according to this invention can efficiently be salted out in such a concentration. While the temperature at the time of salting out by the addition of the halide of an alkali metal of (B) may preferably be as low as possible, a temperature between around 0° and 10° C. is typically adopted. And, when an excess amount of a halide of an alkali metal of (B) is added thereto, a preferred composition according to this invention precipitates. The composition precipitated by salting out can easily be isolated and obtained by a method known per se such as filtration and centrifugal separation. The thus obtained composition is low in explosiveness and can be employed in the same manner for the application of conventional 5-mercapto-1,2,3-thiadiazoles without any danger. The thus obtained composition may be washed by the compound of (A) as occasion demands.

The composition according to the present invention may be prepared by a process which comprises producing a reaction mixture containing a 5-mercapto-1,2,3-thiadiazole formed by conventionally known process for preparing a 5-mercapto-1,2,3-thiadiazole, for instance a method in which chloroacetaldehyde ethoxycarbonylhydrazone is reacted with thionyl chloride followed by mercaptization (above-mentioned Japanese Unexamined Patent Publication No. 23974/1978); a method in which diazomethane and carbon disulfide or its analogue (above-mentioned J. Heterocyclic Chem., 15 1295 (1978)) and other methods; adding optionally to the thus obtained reaction mixture the compound of (A) and/or the halide of an alkali metal of (B); and applying a general precipitating method, for instance, cooling and salting out to precipitate the composition according to this invention. However, in any methods, it is preferable to prepare the composition by a method which comprises obtaining a solution containing a 5-mercapto-1,2,3-thiadiazole in the compound of (A) followed by the addition of the halide of an alkali metal of (B) to salt out the composition according to the present invention.

The composition according to the present invention may be used, for instance, as a raw material for preparing a cepharosporanic acid derivative (see Japanese Unexamined Patent Publication No. 59895/1982 corresponding to U.S. Pat. No. 4,399,132 and British Patent No. 2,083,461) replacing the 5-mercapto-1,2,3-thiadiazole or its salt per se by the present composition.

Next, Synthesis Examples for preparing 5-mercapto-1,2,3-thiadiazoles and Examples of the present invention will be shown below.

In each of the Examples, the hammer-drop sensitivity test and the rubbing sensitivity test were conducted according to JIS-K-4810 testing methods.

SYNTHESIS EXAMPLE 1

After 1 mole (165 g) of chloral hydrate was dissolved in 2 l of methanol, 1 mole (186 g) of p-toluenesulfohydrazide in the form of powder was added to the resulting solution under stirring at room temperature over around 2 minutes, followed by further stirring for 1 hour at room temperature to subject the chloral hydrate to reaction with the p-toluenesulfohydrazide.

Next, while stirring the resulting reaction mixture vigorously, 2.2 moles (528 g) of sodium sulfide nonahydrate was added thereto over around 15 minutes, followed by further stirring for 3 hours to conduct the reaction. Since the addition of sodium sulfide caused generation of heat, the reaction was carried out under ice-cooling so that the reaction temperature might not be more than 40° C. The color of the reaction mixture was reddish brown and sodium chloride was precipitated therein.

After filtration of the precipitated sodium chloride, the filtrate was concentrated to remove the solvent, and the crystals precipitated in the concentrate was collected by filtration followed by recrystallization from a mixed solvent of methanol and methylene chloride to obtain 70 g of sodium salt of 5-mercapto-1,2,3-thiadiazole.

SYNTHESIS EXAMPLE 2

In 200 ml of methanol was dissolved 16.5 g of chloral hydrate. To the resulting stirred solution was added, at around 25° C., 18.6 g of p-toluenesulfohydrazide in the form of powder, followed by further stirring at around 25° C. for 1 hour to subject the chloral hydrate to reaction with the p-toluenesulfohydrazine.

After reaction, while the reaction mixture was stirred vigorously without any isolation of the reaction product, 72.0 g of sodium sulfide nonahydrate was added thereto over around 15 minutes, followed by further stirring at 1 hour at around 25° C. for reaction.

Next, after the reaction mixture was cooled to around −5° C., 4.8 g of bromine was added thereto and the temperature was raised gradually followed by stirring at 20° C. for 40 minutes. The reaction mixture thus stirred presented reddish brown color, and such inorganic salts as sodium chloride, potassium chloride and the like precipitated.

After removal of the precipitated inorganic salt, the solvent was removed from the reaction mixture by distillation under reduced pressure. The thus obtained crude product was recrystallized from a mixed solvent of water, methanol and methylene chloride to obtain 11.4 g of sodium salt of 5-mercapto-1,2,3-thiadiazole dihydrate, of which the yield was 64.7% based on the amount of the starting chloral hydrate.

SYNTHESIS EXAMPLE 3

A reaction was conducted in the same manner as in Synthesis Example 2, except that 2.2 g of chlorine was used in place of the bromine in Synthesis Example 2, to obtain 11.3 g of sodium salt of 5-mercapto-1,2,3-thiadiazole dihydrate. The yield was 64.2% based on the starting chloral hydrate.

SYNTHESIS EXAMPLE 4

A reaction was conducted in the same manner as in Synthesis Example 2, except that 10.9 g of methanesulfohydrazide was used in place of the p-toluenesulfohydrazide in Synthesis Example 2, to obtain 10.2 g of sodium salt of 5-mercapto-1,2,3-thiadiazole dihydrate. The yield was 57.9% based on the starting chloral hydrate.

SYNTHESIS EXAMPLE 5

In 200 ml of methanol was dissolved 16.5 g of chloral hydrate. To the stirred solution was added, at around 25° C., 15.4 g of carboethoxyhydrazine hydrochloride in the form of powder, followed by further stirring at around 25° C. for 1 hour to subject the chloral to reaction with the carboethoxyhydrazine.

After reaction, while stirring the reaction mixture vigorously, 60.0 g of sodium sulfide nonahydrate was added thereto over around 15 minutes followed by further stirring at around 45° C. for 1 hour to carry out the reaction.

In order to control the drastic heat generation, the reaction was conducted under ice-cooling. The color of the resulting reaction mixture was blackish brown, and sodium chloride was precipitated in the reaction mixture.

After removal of the precipitated sodium chloride, the solvent was removed from the reaction system, and the thus obtained crude product was recrystallized from a mixed solvent of methanol, water and methylene chloride to obtain 9.7 g of sodium salt of 5-mercapto-1,2,3-thiadiazole dihydrate. The yield was 55.1% based on the starting chloral hydrate.

SYNTHESIS EXAMPLE 6

A reaction was conducted in the same manner as in Synthesis Example 5, except that 28.0 g of $K_2S$ was used in place of the sodium sulfide nonahydrate in Synthesis Example 5, to obtain 10.2 g of sodium salt of 5-mercapto-1,2,3-thiadiazole dihydrate. The yield was 53.0% based on the starting chloral hydrate.

EXAMPLE 1

In 500 ml of methanol, there were heated under reflux 24.0 g of 5-chloro-1,2,3-thiadiazole and 48.0 g of sodium sulfide ($Na_2S.9H_2O$) to obtain a reaction mixture containing 20.0 g of sodium salt of 5-mercapto-1,2,3-thiadiazole.

From the thus obtained reaction mixture were removed, by filtration, the by-produced precipitate of sodium chloride and the unreacted sodium sulfide; the reaction mixture was further treated with an activated carbon; and then concentrated to 100 ml.

After filtration of the precipitated inorganic salt, 50 ml of water was added to the reaction mixture, and the water-methanol solution containing sodium salt of 5-mercapto-1,2,3-thiadiazole was cooled to 5° C. followed by the addition of 14.9 g of sodium chloride. Upon filtration of the produced precipitate, it was found that the precipitate was a composition containing 22.6 g (70% by weight) of sodium salt of 5-mercapto-1,2,3-thiadiazole dihydrate, 4.9 g (15% by weight) of methanol and water and 4.9 g (15% by weight) of sodium chloride.

In order to know the extent of the explosiveness of the thus obtained composition, the hammer-drop sensitivity test and the rubbing sensitivity test were conducted with respect to the composition according to this invention and the single compound of sodium salt of 5-mercapto-1,2,3-thiadiazole dihydrate. The results are shown in Table 1.

EXAMPLE 2

In 2 l of methanol was dissolved 1 mole (165 g) of chloral hydrate. To the resulting solution under stirring was added 1 mole (186 g) of p-toluenesulfohydrazide in the form of powder at room temperature over around 2 minutes followed by further stirring at room temperature for one hour to subject the chloral hydrate and the p-toluenesulfohydrazide to reaction.

Next, with vigorous stirring of the reaction mixture, 2.2 mole (528 g) of sodium sulfide nonahydrate was added thereto over around 15 minutes and then the stirring was continued for further 3 hours to carry out the reaction. Since the addition of sodium sulfide caused generation of heat, the reaction system was subjected to reaction under ice-cooling so that the reaction temperature during the reaction might not exceed 40° C. The thus obtained reaction mixture colored reddish brown and sodium chloride was precipitated in the reaction mixture.

After removal of the precipiated sodium chloride by filtration, the reaction mixture was concentrated and filtered again to obtain a filtrate. To the filtrate was added 500 ml of an aqueous methanolic solution having a concentration of 6% by weight of methanol to obtain 880 ml of a solution having a concentration of 10% by weight of sodium salt of 5-mercapto-1,2,3-thiadiazole. Next, the solution was treated with an activated carbon, cooled to 5° C. followed by addition thereto of 303 g of sodium chloride. Upon collection by filtration of the precipitate, 114.0 g of a composition consisting of 77.0 g (67% by weight) of sodium salt of 5-mercapto-1,2,3-thiadiazole dihydrate, 17.0 g (15% by weight) of sodium chloride and 20.0 g (18% by weight) of methanol and water.

The results of the hammer-drop sensitivity test and the rubbing test are shown in Table 1.

EXAMPLE 3

In 200 ml of a mixed solution of isopropyl alcohol and water (the content of isopropyl alcohol: 5% by weight) was dissolved 20.0 g of sodium salt of 5-mercapto-1,2,3-thiadiazole dihydrate at 30° C. While cooling the thus obtained solution at 3° C., 69.1 g of sodium chloride was added. Upon addition of the sodium chloride, precipitate was formed which was collected by filtration. It was found that the precipitate is a composition consisting of 17.0 g (70% by weight) of sodium salt of 5-mercapto-1,2,3-thiadiazole dihydrate, 3.16 g (13% by weight) of isopropyl alcohol and water and 4.13 g (17% by weight) of sodium chloride.

The results of the hammmer-drop sensitivity test and the rubbing sensitivity test are shown in Table 1.

EXAMPLE 4

An experiment was run in the same manner as in Example 3 except that 55.5 g of potassium chloride was used in place of the sodium chloride in Example 3 and 200 ml of a mixed solution of ethyl alcohol and water (the content of the ethyl alcohol: 5% by weight) in place of the mixed solution of isopropyl alcohol and water to obtain a composition (27.6 g) consisting of 18.0 g (65.0% by weight) of sodium salt of 5-mercapto-1,2,3-thiadiazole, 4.1 g (15% by weight) of ethyl alcohol and water and 5.5 g (20% by weight) of potassium chloride.

The results of the hammer-drop sensitivity test and the rubbing sensitivity test are shown in Table 1.

and water. The results of hammer-drop sensitivity test and the rubbing sensitivity test are shown in Table 2.

EXAMPLE 6

In 2 l of methanol was dissolved 1 mole (146 g) of chloral. To the stirred resulting solution was added 1 mole (186 g) of p-toluenesulfohydrazide in the form of powder at room temperature over around 5 minutes followed by further stirring at room temperature for 1 hour to subject the chloral and the p-toluenesulfohydrazide to reaction. Next, with vigorous stirring of the resultant reaction mixture, 2.2 moles (172 g) of powdery anhydrous sodium sulfide prepared from hydrogen sulfide and sodium methoxide was added thereto over around 5 minutes followed by stirring for further 2 hours to carry out the reaction. The reaction was carried out under ice-cooling so that the reaction temperature during the reaction might not exceed 40° C. The precipitated sodium chloride in the reaction mixture was removed by filtration and the reaction mixture was

TABLE 1

| Example | Composition of 5-mercapto-1,2,3-thiadiazole (% by weight) | | Hammer-drop sensitivity test (height, cm) | Rubbing sensitivity test (load, kg) |
| --- | --- | --- | --- | --- |
| Examples of the present invention | | | | |
| Example 1 | 5-mercapto-1,2,3-thiadiazole sodium salt dihydrate | 70% | 100 | 8 |
| | water and methanol | 15% | | |
| | sodium chloride | 15% | | |
| Example 2 | 5-mercapto-1,2,3-thiadiazole sodium salt dihydrate | 67% | 90 | 8 |
| | water and methanol | 18% | | |
| | sodium chloride | 15% | | |
| Example 3 | 5-mercapto-1,2,3-thiadiazole sodium salt dihydrate | 70% | 100 | 8 |
| | isopropyl alcohol and water | 13% | | |
| | sodium chloride | 17% | | |
| Example 4 | 5-mercapto-1,2,3-thiadiazole sodium salt dihydrate | 65% | 80 | 7 |
| | ethyl alcohol and water | 15% | | |
| | potassium chloride | 20% | | |
| Comparative Example | | | | |
| | 5-mercapto-1,2,3-thiadiazole sodium salt dihydrate only | | 40 | 4 |

EXAMPLE 5

In 2 l of methanol was dissolved 1 mole (165 g) of chloral hydrate. To the resulting solution with stirring was added 1 mole (186 g) of p-toluenesulfohydrazide in the form of powder at room temperature over around 2 minutes, and the mixture was further stirred at room temperature for 1 hour to subject the chloral hydrate and the p-toluenesulfohydrazide to reaction. Next, while stirring vigorously the reaction mixture, a solution of 2.2 mole (242 g) of potassium sulfide in 400 ml of water was added thereto over around 15 minutes and then the stirring was continued for further 2 hours to carry out the reaction. Since the addition of potassium sulfide caused generation of heat, the reaction was carried out under ice-cooling so that the reaction temperature might not exceed 40° C. After reaction, potassium chloride precipitated and the resultant precipitate was collected by filtration and treated in the same manner as in Example 2 to obtain 126 g of a composition consisting of 86 g (68% by weight) of potassium salt of 5-mercapto-1,2,3-thiadiazole dihydrate, 21 g (17% by weight) of sodium chloride and 19 g (15% by weight) of methanol concentrated to 600 ml. Filtration was carried out again to remove the precipitate and the obtained reaction mixture was treated with an activated carbon followed by cooling at 10° C. and the addition of 28 g of sodium chloride. The formed precipitate was removed by filtration, the precipitate was washed with n-butyl alcohol to obtain 90 g of a composition consisting 63 g (70% by weight) of 5-mercapto-1,2,3-thiadiazole sodium salt, 18 g (20% by weight) of sodium chloride and 9 g (10% by weight) of n-butyl alcohol. The results of the hammer-drop sensitivity test and the rubbing sensitivity test are shown in Table 2.

EXAMPLE 7

After 10 g of potassium salt of 5-mercapto-1,2,3-thiadiazole was dissolved in 400 ml of isopropyl alcohol at 30° C., 2.6 g of sodium chloride was added to the resultant solution while cooling at 5° C. The formed precipitate was filtered to obtain 12.4 g of a composition consisiting of 8.5 g (69% by weight) of potassium salt of 5-mercapto-1,2,3-thiadiazole, 2.5 g (20 by weight) of sodium chloride and 1.4 g (11% by weight) of isopropyl alcohol. The results of the hammer-drop sensitivity test and the rubbing sensitivity test for the present composition are shown in Table 2.

EXAMPLE 8

After 10.0 g of 5-mercapto-1,2,3-thiadiazole dihydrate was dissolved in 50 ml of water at room temperature, 28.1 g of potassium bromide was added thereto while cooling to 0° C. The formed precipate was filtered to obtain 7.6 g of a composition consisting of 5.0 g (66% by weight) of 5-mercapto-1,2,3-thiadiazole dihydrate, 1.4 g (18% by weight) of potassium bromide and 1.2 g (16% by weight) of water. The results of the hammer-drop sensitivity test and the rubbing sensitivity test for the present composition are shown in Table 2.

EXAMPLE 9

After 5.0 g of sodium salt of 5-mercapto-1,2,3-thiadiazole dihydrate was dissolved in 170 ml of methanol at room temperature, 3.4 g of sodium chloride was added thereto while cooling the mixture at 5° C. The formed precipitate was filtered and washed with 50% methanol-toluene solution to obtain 6.5 g of a composition consisting of 4.5 g (67% by weight) of sodium salt of 5-mercapto-1,2,3-thiadiazole dihydrate, 1.0 g (15% by weight) of sodium chloride and 1.2 g (18% by weight) of methanol and toluene. The results of the hammer-drop sensitivity test and the rubbing sensitivity test for the present composition are shown in Table 2.

EXAMPLE 10

An experiment was run in the same manner as in Example 9 except that a 50% methanol-carbon tetrachloride solution was used for washing in place of the 50% methanoltoluene solution to obtain 6.1 g of a composition consisting of 4.3 g (70% by weight) of sodium salt of 5-mercapto-1,2,3-thiadiazole dihydrate, 1.2 g (20% by weight) of sodium chloride and 0.6 g (10% by weight) of methanol and carbon tetrachloride. The results of the hammer-drop sensitivity test and the rubbing sensitivity test for the present composition are shown in Table 2.

EXAMPLE 11

In a 100 ml of a mixed solvent of isopropyl alcohol and water (content of isopropyl alcohol: 5% by weight) was dissolved, at 30° C., 10 g of sodium salt of 5-mercapto-1,2,3-thiadiazole obtained by Synthesis Example 2. While cooling the resulting solution to 3° C., there was added thereto 35 g of sodium chloride. Upon addition of the sodium chloride, there was formed a precipitation which was then collected by filtration to afford 12.1 g of a composition consisting of 8.5 g (70% by weight) of sodium salt of 5-mercapto-1,2,3-thiadiazole dihydrate, 1.6 g (13% by weight) of isopropyl alcohol and water, and 2.0 g (17% by weight) of sodium chloride.

EXAMPLE 12

In a 200 ml of a mixed solvent of isopropyl alcohol and water (content of isopropyl alcohol: 5% by weight) was dissolved, at 30° C., 20 g of sodium salt of 5-mercapto-1,2,3-thiadiazole obtained by Synthesis Example 5. While cooling the resulting solution to 3° C., there was added thereto 69 g of sodium chloride. Upon addition of the sodium chloride, there was formed a precipitation which was then collected by filtration to afford 24.3 g of a composition consisting of 17.0 g (70% by weight) of sodium salt of 5-mercapto-1,2,3-thiadiazole dihydrate, 3.2 g (13% by weight) of isopropyl alcohol and water, and 4.1 g (17% by weight) of sodium chloride.

We claim:

1. A 5-mercapto-1,2,3-thiadiazoles composition consisting essentially of a 5-mercapto-1,2,3-thiadiazole combined with (A) one or more compounds selected from the group consisting of water, an alcohol, an aromatic hydrocarbon and a halogenated hydrocarbon and (B) a halide of an alkali metal; the content of said compound (A) is 5 to 25% by weight and the content of said compound (B) is 10 to 30% by weight of said composition.

TABLE 2

| Example | Composition of 5-mercapto-1,2,3-thiadiazole (% by weight) | | Hammer-drop sensitivity test (height, cm) | Rubbing sensitivity test (load, kg) |
| --- | --- | --- | --- | --- |
| Example 5 | 5-mercapto-1,2,3-thiadiazole potassium salt dihydrate | 68% | 90 | 8 |
| | methanol and water | 15% | | |
| | sodium chloride | 17% | | |
| Example 6 | 5-mercapto-1,2,3-thiadiazole sodium salt | 70% | 100 | 8 |
| | n-butyl alcohol | 10% | | |
| | sodium chloride | 20% | | |
| Example 7 | 5-mercapto-1,2,3-thiadiazole potassium salt | 69% | 100 | 8 |
| | isopropyl alcohol | 11% | | |
| | sodium chloride | 20% | | |
| Example 8 | 5-mercapto-1,2,3-thiadiazole dihydrate | 66% | 80 | 7 |
| | water | 16% | | |
| | potassium bromide | 18% | | |
| Example 9 | 5-mercapto-1,2,3-thiadiazole sodium salt dihydrate | 67% | 90 | 7 |
| | methanol and toluene | 18% | | |
| | sodium chloride | 15% | | |
| Example 10 | 5-mercapto-1,2,3-thiadiazole sodium salt dihydrate | 70% | 100 | 8 |
| | water and carbon tetrachloride | 10% | | |
| | sodium chloride | 20% | | |

2. The 5-mercapto-1,2,3-thiadiazoles composition according to claim 1, wherein the content of the compound of (A) is 10 to 20% by weight and the content of the compound of (B) is 15 to 25% by weight.

3. The 5-mercapto-1,2,3-thiadiazoles composition according to claim 1, wherein the compound of (A) is at least one of water and a saturated aliphatic alcohol and the compound of (B) is at least one of a chloride and bromide of an alkali metal.

4. The 5-mercapto-1,2,3,-thiadiazoles composition according to claim 3, wherein said compound (A) is a saturated aliphatic alcohol selected from the group consisting of methyl alcohol, ethyl alcohol, n-propyl alcohol, isopropyl alcohol, n-butyl alcohol, sec-butyl alcohol and t-butyl alcohol.

5. A process for preparing a 5-mercapto-1,2,3-thiadiazoles composition which comprises steps of adding (B) a halide of an alkali to a solution containing a 5-mercapto-1,2,3-thiadiazole in one or more compounds (A) selected from the group consisting of water, an alcohol, an aromatic hydrocarbon and a halogenated hydrocarbon; precipitating, by salting out, a composition comprising a 5-mercapto-1,2,3-thiadiazole, the compound of (A) and the compound of (B) to obtain the same.

6. The process for preparing a 5-mercapto-1,2,3-thiadiazoles composition according to claim 5, wherein the concentration of the 5-mercapto-1,2,3-thiadiazole contained in the compound of (A) is 3 to 20% by weight.

7. The process for preparing a 5-mercapto-1,2,3-thiadiazoles composition according to claim 6, wherein the concentration of the 5-mercapto-1,2,3-thiadiazole contained in the compound of (A) is 5 to 15% by weight.

8. The process for preparing a 5-mercapto-1,2,3-thiadiazoles composition according to claim 5, wherein the solution containing the 5-mercapto-1,2,3-thiadiazole in (A) one or more compounds selected from the group consisting of water, an alcohol, an aromatic hydrocarbon and a halogenated hydrocarbon is one prepared by subjecting a trihaloacetaldehyde and a hydrazine to condensation reaction using the compound of (A) as a solvent and then to cyclization reaction by the addition, to the resulting reaction mixture, a sulfide, a hydrosulfide or a base and hydrogen sulfide, and subsequently removing insolubles from the thus obtained reaction mixture.

9. The process for preparing a 5-mercapto-1,2,3-thiadiazoles composition according to claim 8, wherein the amount of the hydrazine to be used is around 1.1 molar times the amount of the trihaloacetaldehyde.

10. The process for preparing a 5-mercapto-1,2,3-thiadiazoles composition according to claim 8, wherein the temperature for the reaction of the trihaloacetaldehyde and the hydrazine is in the range of $-20°$ to $50°$ C.

11. The 5-mercapto-1,2,3-thiadiazoles composition according to claim 1, wherein (A) is an aromatic hydrocarbon selected from the group consisting of benzene, toluene, ethylbenzene, xylene and mesitylene.

12. The 5-mercapto-1,2,3-thiadiazoles composition according to claim 1, wherein (A) is a halogenated hydrocarbon selected from the group consisting of methylene, chlorine, chloroform and carbon tetrachloride.

13. The 5-mercapto-1,2,3-thiadiazoles composition according to claim 1, wherein (B) is selected from the group consisting of sodium chloride, potassium chloride, sodium bromide and potassium bromide.

14. The process for preparing a 5-mercapto-1,2,3-thiadiazoles composition according to claim 5, wherein said salting out is at a temperature between about 0 and 10° C.

15. The process for preparing a 5-mercapto-1,2,3-thiadiazoles composition according to claim 5, wherein said halide of an alkali metal is present in excess amount.

16. The 5-mercapto-1,2,3-thiadiazoles composition according to claim 2, wherein component (B) is selected from the group consisting of sodium chloride, potassium chloride, sodium bromide and potassium bromide.

17. The 5-mercapto-1,2,3-thiadiazoles composition according to claim 16, wherein compound (A) is selected from the group consisting of water, methyl alcohol, ethyl alcohol, n-propyl alcohol, isopropyl alcohol, n-butyl alcohol, sec-butyl alcohol and t-butyl alcohol.

18. The 5-mercapto-1,2,3-thiadiazoles composition according to claim 16, wherein compound (A) is an aromatic hydrocarbon selected from the group consisting of benzene, toluene, ethylbenzene, xylene and mesitylene.

19. The 5-mercapto-1,2,3-thiadiazoles composition according to claim 16, wherein compound (A) is a halogenated hydrocarbon selected from the group consisting of methylene, chlorine, chloroform and carbon tetrachloride.

* * * * *